United States Patent
Nicholson et al.

(10) Patent No.: US 8,111,386 B2
(45) Date of Patent: Feb. 7, 2012

(54) MEASURING MODAL CONTENT OF MULTI-MODED FIBERS

(75) Inventors: Jeffrey W. Nicholson, Morristown, NJ (US); Andrew D. Yablon, Livingston, NJ (US)

(73) Assignee: OFS Fitel, LLC, Norcross, GA (US)

( * ) Notice: Subject to any disclaimer, the term of this patent is extended or adjusted under 35 U.S.C. 154(b) by 374 days.

(21) Appl. No.: 12/454,089

(22) Filed: May 12, 2009

(65) Prior Publication Data
US 2009/0262337 A1    Oct. 22, 2009

Related U.S. Application Data

(63) Continuation-in-part of application No. 12/214,629, filed on Jun. 20, 2008, now Pat. No. 7,817,258.

(60) Provisional application No. 61/022,626, filed on Jan. 22, 2008.

(51) Int. Cl.
*G01N 21/00*    (2006.01)

(52) U.S. Cl. ........................................ 356/73.1
(58) Field of Classification Search .................. None
See application file for complete search history.

(56) References Cited

U.S. PATENT DOCUMENTS 6,687,010 B1 * 2/2004 Horii et al. .............. 356/479
7,474,407 B2 * 1/2009 Gutin ..................... 356/479

* cited by examiner

*Primary Examiner* — Tu Nguyen
(74) *Attorney, Agent, or Firm* — Law Firm of Peter V. D. Wilde

(57) ABSTRACT

The output modal content of optical fibers that contain more than one spatial mode may be analyzed and quantified by measuring interference between co-propagating modes in the optical fiber. By spatially resolving the interference, an image of the spatial beat pattern between two modes may be constructed, thereby providing information about the modes supported by the optical fiber. Measurements of the phase front exiting the optical fiber under test are advantageously performed in the far field.

19 Claims, 7 Drawing Sheets

MEASURING MODAL CONTENT OF MULTI-MODED FIBERS

RELATED APPLICATION

This application is a Continuation-In-Part of application Ser. No. 12/214,629 filed Jun. 20, 2008 now U.S. Pat. No. 7,817,258, claiming the benefit of U.S. Provisional Application No. 61/022,626, filed Jan. 22, 2008, which applications are incorporated herein by reference.

FIELD OF THE INVENTION

This invention relates to analyzing the optical properties of optical waveguides. More specifically it relates to methods and apparatus for measuring mode patterns and power levels in multi-mode optical fibers.

BACKGROUND OF THE INVENTION

Optical fiber lasers are desirable for their excellent beam quality, even when operating at high power. The quality of a beam emitted from an optical fiber is frequently quantified using the measure "$M^2$", which is a measure of how tightly the beam can be focused in free space. A beam with a perfect Gaussian spatial profile has a theoretical $M^2$ value of one. A problem with applying $M^2$ measurements to optical fibers is that large mode area fibers typically support several modes, and $M^2$ can be relatively insensitive to the amount of power in a higher order mode. $M^2$ is even less useful, and potentially confusing, when propagation in a higher order mode (HOM) is intentional, as individual HOMs have inherently high values of $M^2$. Therefore new measurement techniques capable of quantifying the modal content of fibers that support more than one mode are needed.

SUMMARY OF THE INVENTION

We have developed a technique for analyzing and quantifying the output modal content of optical fibers that support more than one spatial mode. The technique is based on measuring interference between co-propagating modes in the optical fiber. By spatially resolving the interference, an image of the spatial beat pattern between two modes is constructed, thus providing information about the modes that are propagating in the optical fiber.

BRIEF DESCRIPTION OF THE DRAWING

The invention may be more easily understood with the aid of the drawing, in which.

DETAILED DESCRIPTION

In the context intended for this discussion, the subject optical fibers are typically few mode fibers but are referred to here as multi-mode fibers. In typical applications wherein specific modes are characterized, the number of modes propagating in the optical fiber may be few. However, applications may arise where the optical fiber supports many modes but just one, or a few, or even mode groups, may be the subject of the analysis. In some situations, the fiber may be nominally singlemode and a method is desired to analyze the characteristics of weakly guided or weakly radiated higher order modes.

Figure 1:
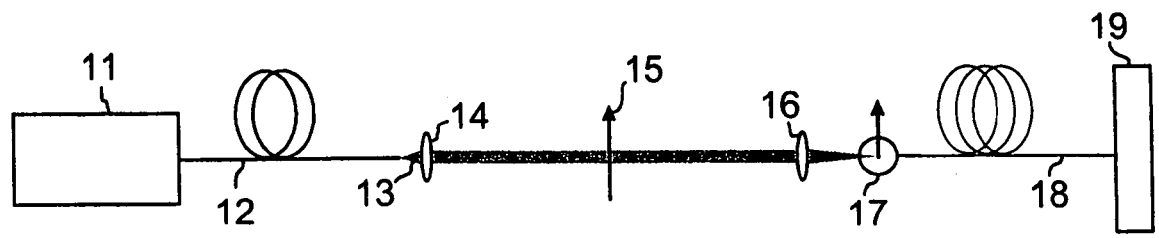
FIGS. 1 and 2 show experimental setups for spatially resolved spectral interferometry measurements useful for characterizing modal content of multi-mode fibers. The arrangement of FIG. 1 has an imaging lens arrangement for focus and magnification. The measurement apparatus of FIG. 2 is designed for proximity measurements.

A schematic of one particular implementation of the measurement technique of the invention is illustrated in FIG. 1. Light from an optical source 11, having a broad bandwidth (few tens of nanometers, or more) such as an amplified spontaneous emission source (ASE), is launched into an optical fiber 12. The optical fiber 12 is the fiber under test and is typically a large-mode-area (LMA) fiber that supports multiple transverse modes. At the exit of the fiber, the light is re-imaged onto the tip of single mode fiber 18. The light collected by the single mode fiber is measured using detector 19, which in the embodiment shown is an optical spectrum analyzer (OSA). The imaging system used in this embodiment comprises imaging lenses 14 and 16, and a polarizer 15. The polarizer 15 ensures polarization mode alignment and the single mode fiber 18 ensures modal overlap in the OSA. If desired, the focal lengths of the imaging lenses can be chosen to magnify the image. If the optical fiber being analyzed is polarization maintaining, the polarizer may not be necessary. However a polarizer may still be used to analyze any residual light launched into the non-desired polarization state.

Figure 2:
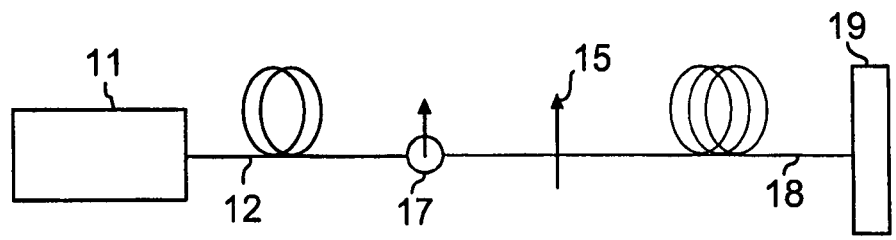

In a slightly modified alternative embodiment, shown in FIG. 2, the imaging lenses are removed, and the single mode fiber is placed in close proximity to the LMA fiber. In both setups fiber ends may be cleaved, polished, or even connectorized. It may be inferred from comparing FIGS. 1 and 2 that the polarizing element may be placed at any point between the output of the LMA fiber and the detector.

If the light exiting the LMA fiber is single moded, then the spectrum measured by the OSA simply reflects the power spectrum of the broadband source. However, if multiple modes are propagating in the LMA fiber, they will each have slightly different group delays and consequently will interfere at the output of the fiber. As a result, a spectral interference pattern, related to the beating of the modes, is measured in the OSA.

Figure 3:
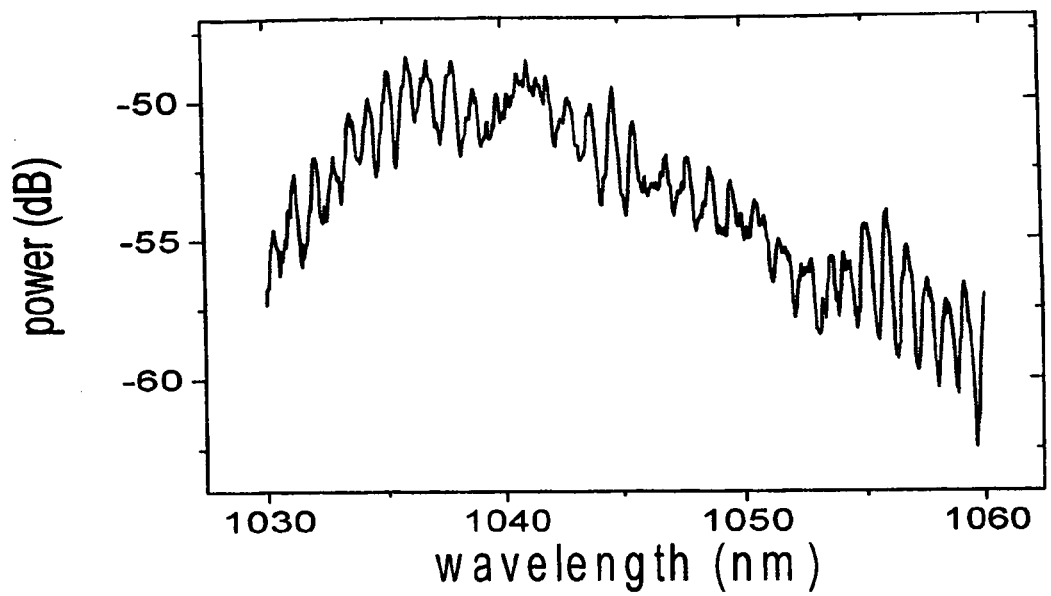
FIG. 3 is a plot of wavelength vs. power showing an output light intensity spectrum measured at detector 19 in FIG. 1 or 2.
Figure 4:
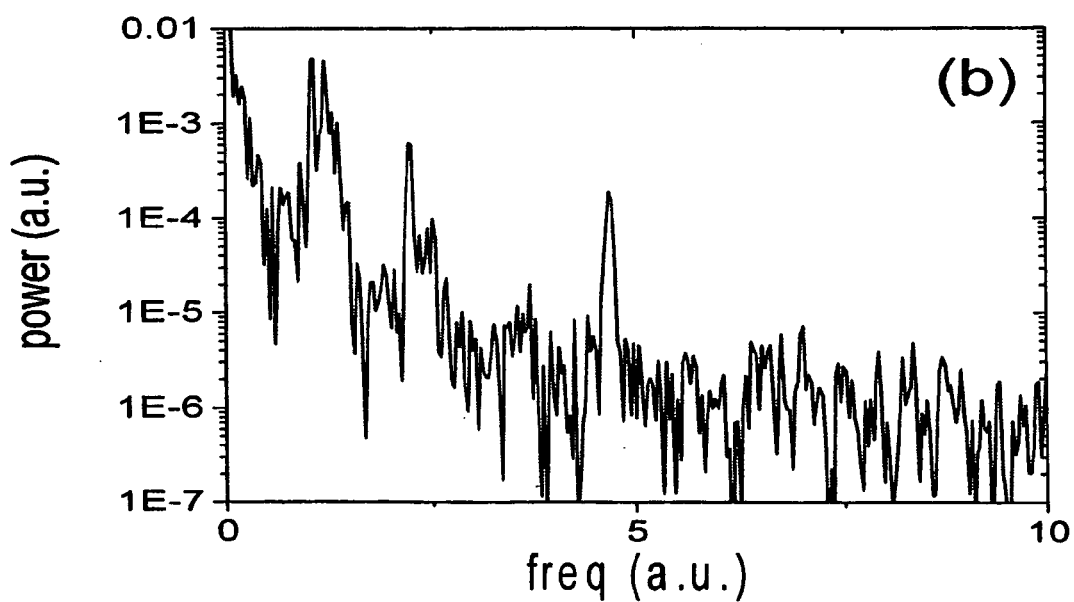
FIG. 4 shows the Fourier transform of the spectrum of FIG. 3.

The single mode probe fiber is assumed to sample only a small portion of the near-field image of the beam from the fiber under test. Therefore the end of the single mode fiber may be placed on a scanning X-Y stage 17 (FIGS. 1 and 2) and the position of the fiber end is raster scanned with respect to the position of the beam and at each x and y position of the single mode fiber tip an optical spectrum is measured. FIG. 3 shows a representative measurement of the spectrum from the single mode fiber at an arbitrary (x,y) point. The spectrum shows clearly visible mode beats. By Fourier transforming the spectrum with respect to optical frequency the spectrum of FIG. 4 results. The spectrum in FIG. 4 shows well defined peaks, with each peak corresponding to beating between a different set of modes. Therefore, by measuring the spectrum at each x and y point, and Fourier filtering, the spatial pattern of the beat between two different transverse modes can be obtained. The measurements provide information for both identification of the modes propagating in the fiber, and quantification of the relative power in each mode.

To demonstrate the measuring method of the invention, results from a 20 µm mode-field diameter, Yb doped fiber are given. The measurements were obtained using the set up shown in FIG. 1, with a 6 m length of LMA Yb-doped fiber, and an Yb amplified spontaneous emission (ASE) source for broadband input light. Imaging lenses magnified the near-field image of the beam, and 980-nm single mode fiber (SMF) was used as a probe fiber. The SMF was raster scanned in x and y, and a set of 32×32 optical spectra were collected.

Figure 5:
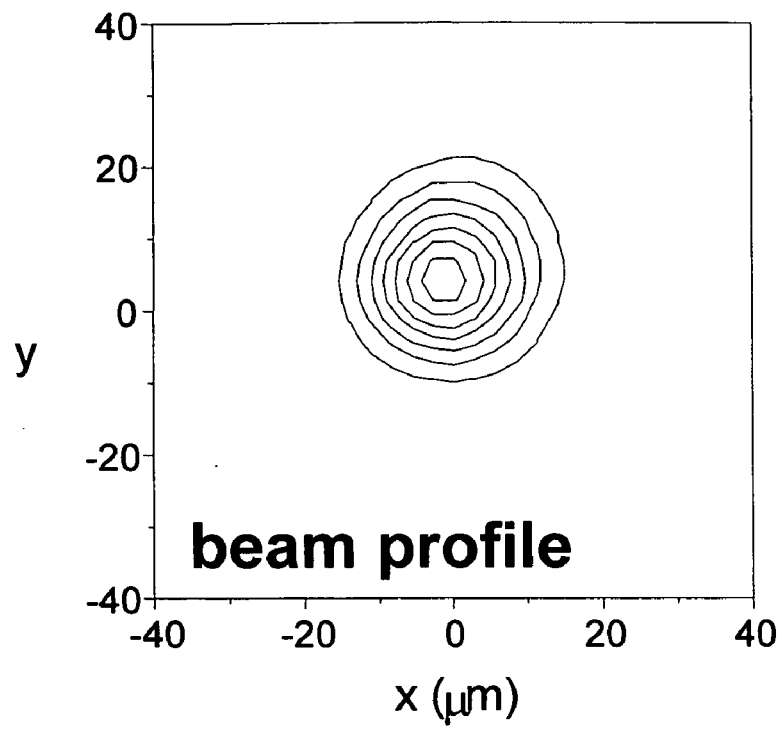
FIG. 5 is a beam profile obtained by integrating the spectrum at each x,y, point using the measurement apparatus of FIG. 1 or 2.

When the optical spectrum at each (x,y) point is integrated, an image of the beam profile is obtained from the data. This image is shown in FIG. 5, showing a primarily Gaussian shaped mode. The $M^2$ of this fiber was measured to be approximately 1.1. This value for $M^2$ is consistent with the value for $M^2$ predicted for the fundamental LP01 mode.

Figure 6:
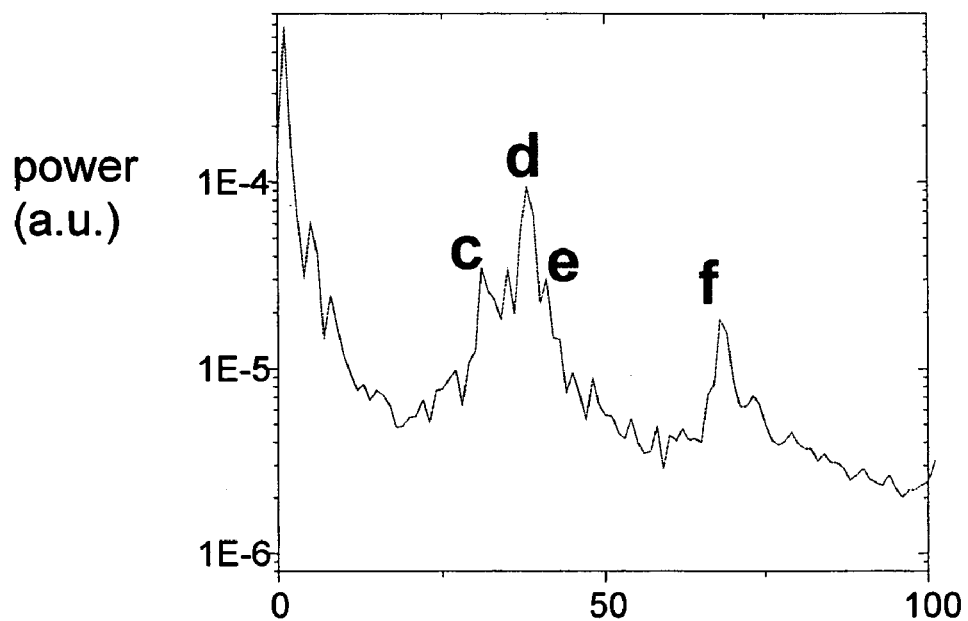
FIG. 6 is a power spectrum derived by Fourier transforming data collected from measurements illustrated in FIGS. 5 and 7-10.
Figure 7:
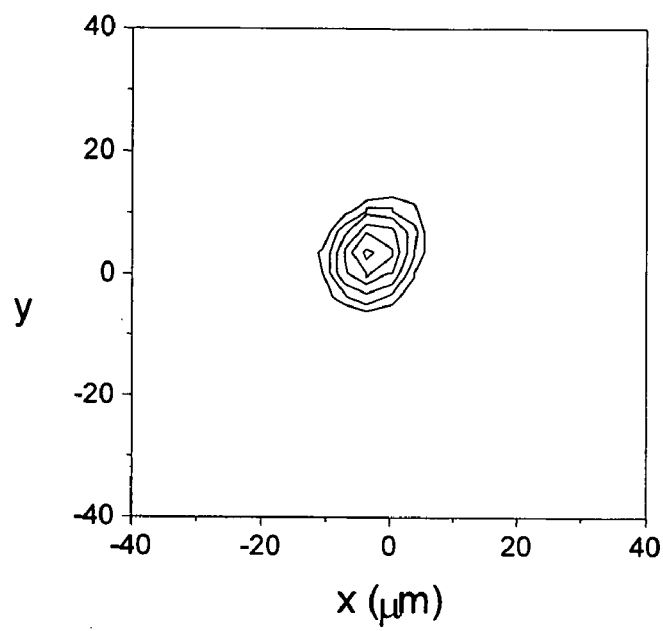
FIGS. 7-10 are images and relative power levels of higher-order modes obtained using the measurement apparatus of FIG. 1 or 2.
Figure 8:
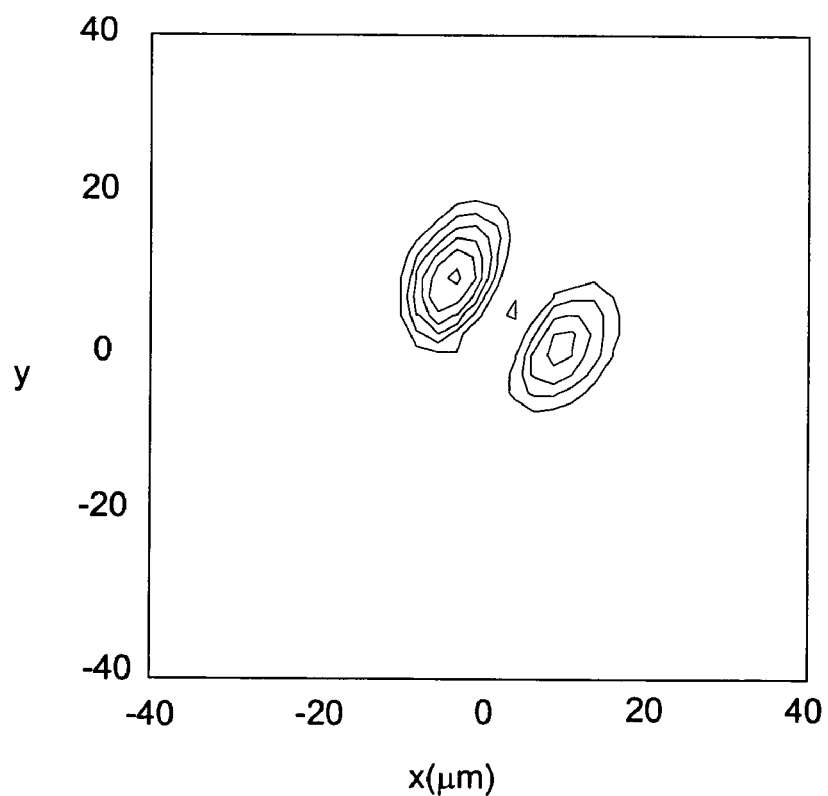
Figure 9:
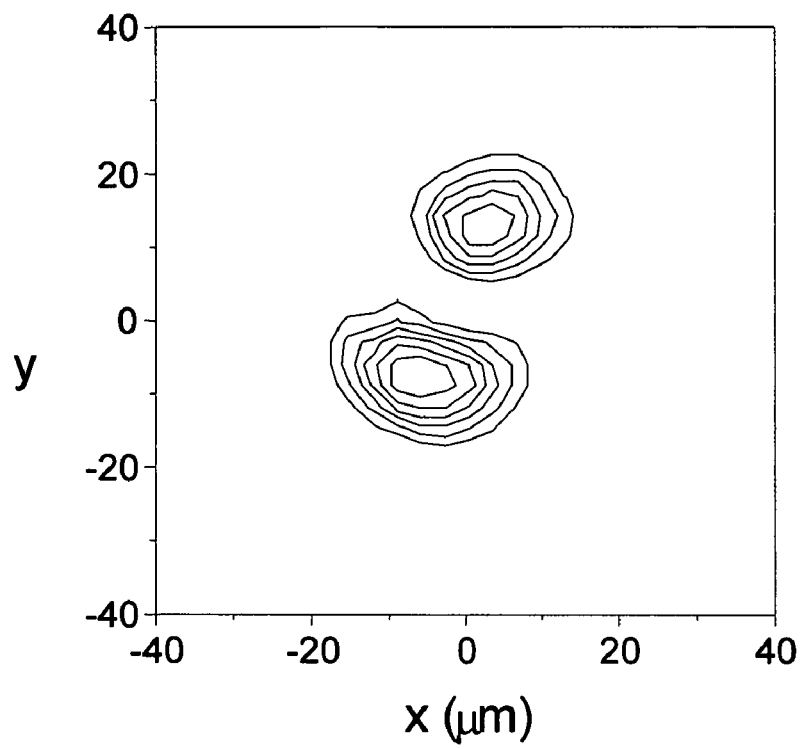
Figure 10:
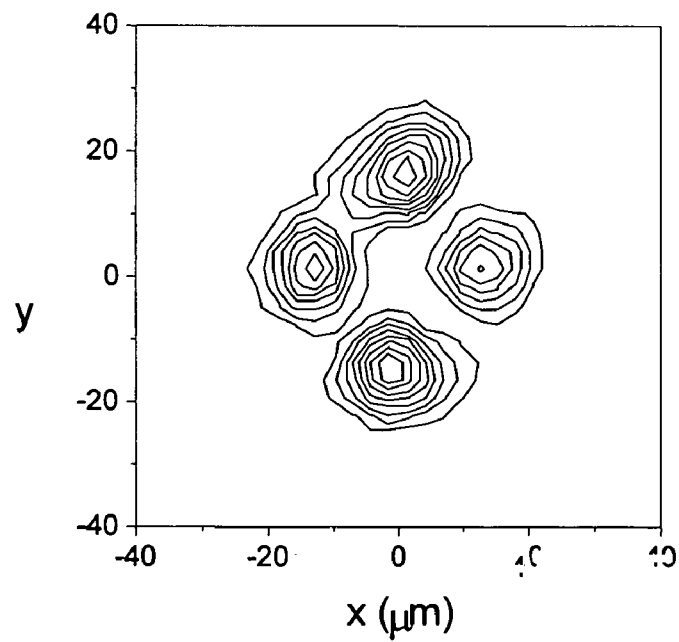

The spectrum at each point was Fourier transformed, and all of the measured spectra were averaged together to give the plot shown in FIG. 6. Although most of the optical power in the fiber is contained in the fundamental, $LP_{01}$, mode, multiple beat frequencies clearly indicate the presence of more than one higher order mode.

To quantify the modal content the value of the Fourier transform at a given Fourier frequency was recorded for every (x,y) point, and normalized to the value of the Fourier transform at zero frequency as described below in the discussion of data analysis. This calculation gives the strength of the interference term between the two modes. From this term the relative strength of the two fields and spatial pattern is obtained.

Results for the strongest of the peaks visible in the Fourier transform of the spectrum are shown in FIGS. 7-10. For example, when the Fourier transform is filtered at the peak labeled 'c' in FIG. 6, the resulting calculation shows an image (FIG. 7) of an $LP_{02}$ mode, with a power of 24 dB weaker than the power contained in the fundamental mode. Two closely spaced peaks labeled 'd' (FIG. 8) and 'e' (FIG. 9) both correspond to $LP_{11}$ modes, but the two are rotated with respect to each other by 90 degrees. The peak labeled 'd' is the strongest observed higher-order-mode, with a power 15.5 dB down from the power in the fundamental mode. The image of the mode with beat frequency corresponding to 'f' (FIG. 10) clearly shows an $LP_{21}$ mode with power 29 dB down from the fundamental mode. Other modes with even weaker power are also visible as additional peaks.

As should be evident this measurement method readily identifies the modes propagating in the fiber while also quantifying the level of modal multipath interference (MPI).

The mode image and MPI from the Fourier transform can be determined using the following.

Two beam interference between electric fields with amplitudes $A_1(x,y,\omega)$ and $A_2(x,y,\omega)$ is considered. If both fields are assumed to have the same frequency dependence than the two fields are related by $$A_2(x,y,\omega)=\alpha(x,y)A_1(x,y,\omega).$$

When the two fields interfere on a detector the resulting spectral intensity is $$I(x,y,\omega)=I_1(x,y,\omega)[1+\alpha^2(x,y)+2\alpha(x,y)\cos(\alpha\omega)],$$

where the phase difference between the two modes, aω, is assumed to be a linear function in frequency. By integrating the measured spectral intensity over ω, $I_1(x,y)$ and $I_2(x,y)$ are related to the total spectral intensity by $$I_1(x, y) = \frac{I(x, y)}{1 + \alpha^2(x, y)},$$

and $$I_2(x, y) = \frac{\alpha^2(x, y)I(x, y)}{1 + \alpha^2(x, y)}.$$

This assumes that the many periods of the beat frequency are contained within the measurement window of the spectrometer, and that $I_1(x,y,\omega)$ is slowly varying in frequency. The total MPI is the ratio of the two intensities, integrated over the beam.

$$MPI = 10\log\left[\frac{\int\int I_2(x, y)dxdy}{\int\int I_1(x, y)dxdy}\right].$$

Experimentally, the measurement of MPI is made by extracting the quantity $\alpha(x,y)$ from the Fourier transform of the measured spectral intensity, $I(x,y,\omega)$. The Fourier transform of $I(x,y,\omega)$ with respect to ω is $$\mathfrak{I}\{I(x,y,\omega)\}=B(x,y,u)=(1+\alpha^2)B_1(x,y,u)+\alpha(B_1(x,y,u-\alpha)+B_1(x,y,u+\alpha)),$$

where u is the Fourier transform coordinate of ω, and $B_1(x,y,u)$ is the Fourier transform $I_1(x,y,\omega)$. Assuming the peaks are well separated, the ratio of the peaks at u=0 to u=a is therefore $$\frac{B(x, y, u = a)}{B(x, y, u = 0)} = f(x, y) = \frac{\alpha(x, y)}{1 + \alpha^2(x, y)}$$

The fraction f(x,y) is calculated from the ratios of the value of the Fourier transformed spectral intensity at the desired spectral peak to the DC value. From f(x,y), $\alpha(x,y)$ can be calculated at each (x,y) point:

$$\alpha(x, y) = \frac{1 - \sqrt{1 - 4f^2(x, y)}}{2f(x, y)}$$

Note that the above algorithm deals with extracting the intensity profile of the mode. Higher order modes in fibers also contain unique phase profiles. For example the two lobes of the $LP_{11}$ mode have a pi phase difference between them. The phase difference between the modes is readily obtainable from the data from the Fourier transform. Consequently by simply Fourier transforming the optical spectra at each x-y point and making note of the phase at a given Fourier frequency, phase images of higher order modes can be obtained.

A generalized measurement setup may be described as basically that shown in FIGS. 1 and 2 except that the detector may be a detector with frequency resolution matched to the optical source. A computer may be used to perform automated scanning of the spatial filter, and data acquisition from the detector. The near field image of the fiber may be magnified using imaging optics (FIG. 1) or the spatial filter may be placed in close proximity to the fiber output (FIG. 2). In either case, for achieving good spatial resolution the spatial filter is preferably smaller than the spatial features of the optical mode.

Polarization overlap at the detector is desirable. A polarizer in the beam forces polarization overlap. If the modes are not already co-polarized, measurements may be made with two different alignments of the polarizer to quantify the MPI and relative polarizations of the modes.

In the experiments described above, a single-mode fiber was used to sample a small portion of the beam from the fiber under test. Alternatively, a pinhole with imaging optics to couple the light from the pinhole to the OSA may be used.

A variety of alternatives exist for the combination of broadband optical source and detector. For characterization of long fibers it may be useful to operate the method in the electrical domain, with a DFB laser as a broadband source (for example) and a photodiode plus RF electrical spectrum analyzer to obtain frequency resolution. A laser with frequency tunability coupled with a power meter or photodetector provides broadband operation and high frequency resolution. For even simpler operation, a tunable laser, serving as a broadband source, plus a camera, such as a CCD, provides a simple setup and eliminates the need for a separate spatial filter element. Other alternative arrangements are:

1. using a bulk optic spatial filter, rather than an SMF fiber in front of the optical detector;
2. as an alternative to scanning the position of the spatial filter, the beam may be translated in the focal plan by scanning the position of the end-face of the multi-mode fiber under test, scanning the focusing or collimating optics, or using a turning mirror or lens that can be suitably tilted;
3. using computers and/or application specific ICs or circuit boards for automated data acquisition and hardware control of the optical source, optical detection, and or scanning equipment;
4. using a computer and software algorithm to process the data and calculate the MPI levels of the various modes. A suitable algorithm for analyzing the data is described above, but it is recognized that there are many possible computer algorithms for analyzing the data.

All these methods share the common function of sampling sequential portions of the output test beam by sampling a portion of the beam from the fiber under test and analyzing the sequential portions using an optical detector. Sequential portions are portions in space, typically x-y space, that are sequentially analyzed as a function of frequency. In some embodiments the broadband source emits a band of wavelengths and the frequency dependence of the transmission through the fiber under test is analyzed using an optical detector with frequency discrimination. In other embodiments the frequency dependence of the transmission through the fiber under test is analyzed by tuning a broadband source through a band containing individual wavelengths and measuring the power of the source at each individual wavelength.

In the technique described above the multi-mode fiber to be characterized functions as an interferometer in which low powers in unwanted modes are generated at a few discrete scattering points such as at splices or at the launch into the fiber. Because the measurement relies on a well defined Fourier peak it is dependant on discrete multi-path interference (MPI). MPI is defined as the ratio of power between two modes in a dB scale. The technique is most effective when multiple higher order modes are generated by scattering at a few discrete sites in the fiber under test, for example, at splices or at the insertion point of the fiber. Another aspect, however, is distributed MPI, in which modes are generated through scattering continuously along the fiber length. Distributed MPI can also be quantified with this technique, and is identifiable as it creates a broad plateau in the frequency spectrum for the mode beats, rather than the sharp peak caused by discrete scattering. Incoherent light, such as that produced by ASE in an amplifier, may also be more difficult to quantify by the measurement described above. To address this, the method may be modified by quantifying the coherence of the fundamental mode of the fiber.

Figure 11:
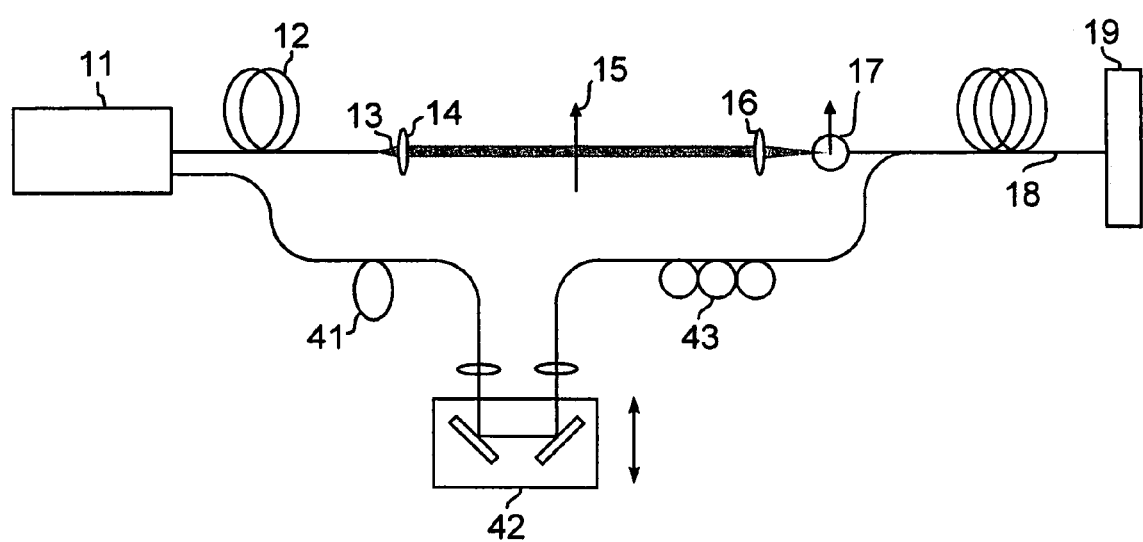
FIG. 11 is an alternative measurement apparatus for adding measurements of spatially resolved coherence.

FIG. 11 is a schematic of a suitable setup for the modified measurement. The optical fiber to be characterized and the scanning spatial filter are placed in one arm of a Mach-Zender interferometer. A single mode fiber 41, a variable delay element 42, and polarization control means 43 are placed in the other arm. The variable delay allows the group delay between the desired mode of the fiber under test and the single mode arm of the interferometer to be placed at an arbitrary offset. Incoherent light in modes other than the mode to be characterized produces a spatial pattern in the coherence of the mode. Polarization control produces polarization overlap at the output of the interferometer, while the spatial filter, here shown as a single-mode fiber, ensures modal overlap at each (x,y) point.

It is evident from the foregoing description, and the embodiment represented generally by FIG. 1, that it is convenient to measure the spatially dependent interference pattern of the output beam from the spatial filter, in this case a few mode fiber, in the near field, i.e., in the image plane of the optical system used for imaging the output of the fiber under test. With this measurement method, the phase front of the beam exiting the end surface of the optical fiber is planar. However, effective measurements may also be made in the far field. This follows from the independent discovery that when the output beam from the spatial filter undergoes diffraction into the far field, and the phase front develops a curvature, all the modes have undergone an equivalent Fourier transform and the mode relationship along the curved phase front is representative of that along the x-y plane at the near field output of the spatial filter.

Figure 12:
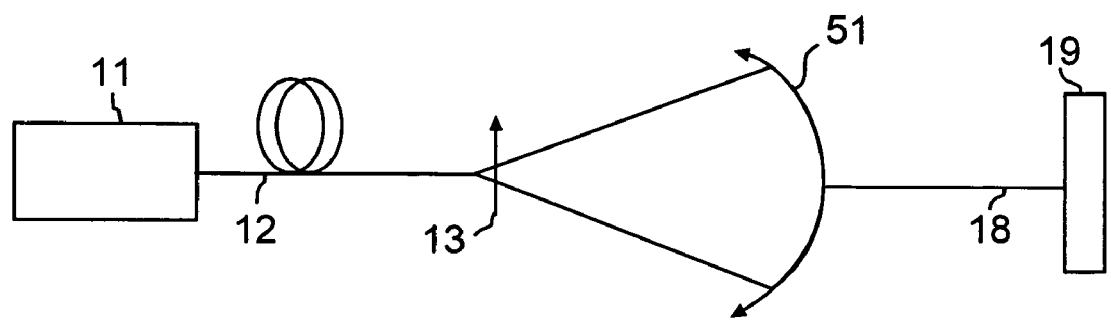
FIGS. 12 and 13 show experimental setups, similar to that of FIG. 1, for spatially resolved spectral interferometry measurements in the far field.
Figure 13:
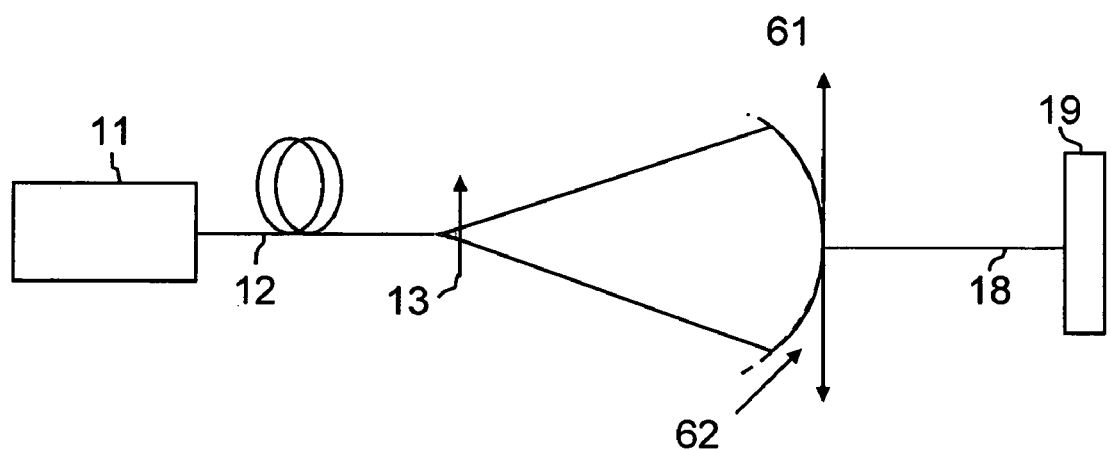

FIGS. 12 and 13 show experimental setups, similar to that of FIG. 1, for spatially resolved spectral interferometry measurements in the far field. FIG. 12 shows the output of the optical fiber under test 12 diffracting into the far field. The phase front in the far field is curved as shown. A detector 18,19, with wavelength resolution is used that effectively scans the output along a suitable arc 51. The detector may be, for example, the tip of an optical fiber moving in an arc. The figure shows the scan in one dimension but it will be understood that the scan actually proceeds in two dimensions. The simplest scan mode is one where the detector remains equidistant from the optical fiber output during the scan. That results, for example, when the detector scans over a spherical arc and the focal point of the spherical arc is at or near the optical fiber end. Using multiple detectors in a spherical array, for example, a photodiode array, removes the need for moving elements. The photodiode array may be an array of simple photodiodes without wavelength resolution. The wavelength spectrum in this case may be generated with a tunable wavelength source.

As mentioned earlier a CCD imaging device is a desirable alternative, and removes the need for moving elements. In that case the entire x-y dependence of the intensity of the beam at a single wavelength is measured at once, and thus provides a fast response. However, this choice of measurement requires a tunable laser to produce a wavelength spectrum. The stability of the tunable laser may become an issue. Drift in the wavelength of the laser during the measurement may cause inaccurate results. In contrast, measuring pixels individually with a scanning fiber probe, for instance in the method described by FIG. 12, has relaxed requirements in terms of the phase stability between various modes in the fiber. To measure the frequency of the spectral beat note the phase between modes should be stable during the duration of the optical spectrum measurement. However, since the relevant data is the amplitude of the spectral beat note for a given individual pixel, drift of the phase between the modes from one pixel to another may be tolerated when the beam is measured using a scanning fiber probe.

When the beam is measured using a CCD, all the pixels are measured at once, then the wavelength of the tunable laser is incremented and the beam is measured again. In this configuration, the phases between the modes should therefore remain stable for the duration of the entire measurement. Assuming a CCD camera that acquires 10 frames per second, for example, with 1000 wavelength points being measured, the phases should remain stable for 100 seconds.

In an alternative method of using multiple detectors in a spherical array, the photodiode array may be an array of simple individual photodiodes wired to a data acquisition device.

Another alternative to moving the detector is to move the light beam exiting from the optical fiber output using beam steering optics to scan the beam in a raster over a stationary detector. Beam steering optics for raster scanning may be refractive or reflective.

Another option is represented by FIG. 13, where the scan of the optical beam from the optical fiber 12 is implemented in an x-y plane. FIG. 13 shows the detector scanning in x-y plane 61. Since the distance 62 between the phase front and the x-y plane varies, a correction factor is used in conjunction with the detector to compensate for the varying distance.

Other options for detecting in variations in the optical output along the curved far field phase front may occur to those skilled in the art. The far field is where the beam has undergone substantial diffraction. In the far field, the spatial intensity profile of the beam is the spatial Fourier Transform of the intensity profile at the exit from the optical fiber. As the beam diffracts it typically will have a curved phase front. A substantially curved phase front is easily discerned by optical elements, detector elements, or software, in the measuring method that compensate for curvature in the phase front of the optical beam being measured.

To increase diffraction of the output test beam, or otherwise shape the beam in the far field, a suitable lens or lens system may be inserted at or near the output of the optical fiber under test. Optical lens systems may be designed that produce a planar wave front in the far field.

Multimode fiber that is the subject of the foregoing description can be recognized as generally having a relatively large core diameter, typically greater than 10 microns. This property distinguishes the optical fiber from single mode optical fiber that typically has a core diameter of 6 microns or less. A multi-mode optical fiber in the context of the invention is an optical fiber that supports more than one transverse mode.

Light propagating in an optical fiber generates a group delay difference between the modes which have a beat frequency in the optical spectral equal to 1/(group delay difference). The optical fiber length should be long enough to produce a beat frequency which is at half the optical bandwidth of the source being used. The optical fiber length should be short enough that the beat frequency is at least twice the resolution bandwidth of the optical detector being used.

A broadband source is defined as a light source having a wavelength broader than at least twice the beat frequency of the group delay difference to be characterized. The beat frequency between the modes is determined as 1/(difference in group delay between the modes). The broadband source may be a device that emits light over a broad wavelength band or a device that can be tuned to several or many wavelengths over a broad wavelength band. In the former case, a frequency selective detector is used to discriminate wavelengths at the detection end. In the latter case the frequency selection is made at the input end, and a wavelength selective detection means is not need at the detection end.

The invention has been described in the context of optical fibers, and this context is expected to be the most relevant in commercial practice. However, the principles apply to other forms of optical waveguides, for example, waveguides in planar optical integrated circuits.

In summary the method of the invention involves the steps of passing light from a broadband source through a length of multi-mode waveguide under test to produce an output test beam, and analyzing discrete portions of the output test beam using a photodetector located in the near field or far field. The portion of the test beam may be generated using a single mode fiber to sample a portion of the beam from the fiber under test and scanning the single mode fiber in the x-y plane, with the x-y plane approximately normal to the direction of the test beam. Or the wave front of the output test beam may be measured in the far field as described above.

In concluding the detailed description, it should be noted that it will be obvious to those skilled in the art that many variations and modifications may be made to the preferred embodiment without substantial departure from the principles of the present invention. All such variations, modifications and equivalents are intended to be included herein as being within the scope of the present invention, as set forth in the claims.

The invention claimed is:

1. A method for characterizing the modes propagating in an optical waveguide comprising the steps of:
   passing light from a broadband source through a length of optical waveguide to produce an output beam,
   sampling sequential portions of the output beam in two dimensions by placing an aperture in a far field of the output beam, and scanning a spatial position of the aperture relative to the output beam in two-dimensions; and
   analyzing a wavelength dependence of light exiting the aperture at a plurality of spatial sampling points using an optical detector with wavelength discrimination.

2. The method of claim 1 wherein the broadband source is selected from the group consisting of a light emitting diode, an amplified spontaneous emission light source, a supercontinuum light source, and any white-light source.

3. The method of claim 1 wherein the waveguide is the core of an optical fiber.

4. The method of claim 1 wherein the aperture is a single-mode fiber.

5. The method of claim 4 wherein the aperture scans in an arc and the arc corresponds to the curvature of the optical wavefront.

6. The method of claim 5 wherein the arc is at an approximate focal length with respect to an end of the optical fiber.

7. The method of claim 4 further comprising the step of reshaping the optical wavefront to produce a planar wavefront in the far field.

8. The method of claim 1 wherein the output beam has a wavefront with curvature and the method further comprises the step of compensating for the curvature.

9. The method of claim 8 wherein the aperture scans in an x-y plane.

10. The method of claim 9 further comprising the step of compensating for a difference between the curved wavefront and the x-y plane.

11. The method of claim 1 wherein the broadband source is a tunable wavelength source.

12. The method of claim 1 wherein the optical detector has frequency discrimination.

13. The method of claim 12 wherein the optical detector is an optical spectrum analyzer.

14. The method of claim 12 wherein the optical detector comprises a photodiode and an electrical spectrum analyzer.

15. The method of claim 1 wherein the output beam is analyzed using a photodiode array.

16. A method for characterizing the modes propagating in an optical waveguide comprising the steps of:
    passing light from a broadband source through a length of optical waveguide to produce an output beam,
    sampling sequential portions of the output beam in two dimensions by placing an aperture in a far field of the output beam, wherein the aperture has a fixed spatial position;
    moving the output beam over the aperture;
    scanning the movement of the output beam; and
    analyzing wavelength dependence of light exiting the aperture at a plurality of spatial sampling points using an optical detector with wavelength discrimination.

17. The method of claim 16 wherein the step of scanning further comprises raster scanning the movement of the output beam.

18. The method of claim 16 wherein the step of moving further comprises the step of moving an output tip of the optical waveguide.

19. The method of claim 16 wherein the step of moving further comprises the steps of:
    bouncing the output beam off a disposed mirror; and
    adjusting a tilt of the mirror.

* * * * *